(12) United States Patent
Blue

(10) Patent No.: US 9,615,954 B2
(45) Date of Patent: Apr. 11, 2017

(54) FLEXIBLE HAND AND WRIST BRACE

(76) Inventor: Tina Ruth Blue, St. Thomas, VI (US)

(*) Notice: Subject to any disclaimer, the term of this patent is extended or adjusted under 35 U.S.C. 154(b) by 740 days.

(21) Appl. No.: 13/565,860

(22) Filed: Aug. 3, 2012

(65) Prior Publication Data

US 2014/0039372 A1 Feb. 6, 2014

(51) Int. Cl.
*A61F 5/01* (2006.01)
*A61H 1/02* (2006.01)
*A41D 19/00* (2006.01)

(52) U.S. Cl.
CPC ........ *A61F 5/0118* (2013.01); *A41D 19/0044* (2013.01); *A61H 1/02* (2013.01)

(58) Field of Classification Search
CPC ..................................................... A61F 5/0118
USPC . 602/21, 20, 5, 1, 64, 62, 61, 60, 41; 2/159, 2/161.1, 161.2, 161.4, 162, 170, 908, 910, 2/917; D24/190–191; 128/878–879
See application file for complete search history.

(56) References Cited

U.S. PATENT DOCUMENTS

| | | | | |
|---|---|---|---|---|
| 3,238,939 A | * | 3/1966 | Stubbs | A63B 71/146 128/DIG. 15 |
| 3,512,776 A | * | 5/1970 | Thomas, Sr. | A41D 13/088 2/161.7 |
| 3,598,408 A | * | 8/1971 | Klose | 473/62 |
| 3,815,908 A | * | 6/1974 | Hashimoto | A63B 71/148 128/DIG. 15 |
| 4,309,991 A | * | 1/1982 | DeMarco | A61F 13/108 473/62 |
| 4,584,993 A | | 4/1986 | Nelson | |
| 4,958,384 A | * | 9/1990 | McCrane | 2/161.6 |
| 5,267,943 A | * | 12/1993 | Dancyger | 602/5 |
| 5,313,667 A | * | 5/1994 | Levine | 2/16 |
| 5,417,645 A | | 5/1995 | Lemmen | |
| 5,513,657 A | * | 5/1996 | Nelson | A61F 5/0118 128/879 |
| 5,538,501 A | * | 7/1996 | Caswell | 602/64 |
| D381,128 S | | 7/1997 | Caswell et al. | |
| 5,787,896 A | | 8/1998 | Sackett | |
| 5,819,313 A | * | 10/1998 | McCrane | A41D 13/088 2/16 |

(Continued)

OTHER PUBLICATIONS

DonJoy Boomerang Wrist Brace, available at http://www.braceshop.com/productcart/pc/DonJoy-Boomerang-Wrist-Brace-60p654.htm.

(Continued)

*Primary Examiner* — Tarla Patel
(74) *Attorney, Agent, or Firm* — The Concept Law Group, P.A.; Scott D. Smiley; Erin A. Martin

(57) ABSTRACT

A hand-and-wrist brace that includes a body having first and second support members, both having inner and outer surfaces, the first support member having a first position along a wrist support path where the left and right ends are uncoupled and a second position along the wrist support path where the left and right ends are coupled to substantially encapsulate a user's wrist, and the second support member having a proximal end, a distal end, extending outwardly from and coupled to an upper end of the first support member, having a first position along a secondary support path with distal end uncoupled to the first support member, and having a second position along the secondary support path with the distal end being removably-couplable to a plurality of locations on the outer surfaces of both the first support member and the second support member.

18 Claims, 7 Drawing Sheets

(56) References Cited

U.S. PATENT DOCUMENTS

| | | | |
|---|---|---|---|
| 5,873,130 A | 2/1999 | Lafferty | |
| 6,142,966 A | 11/2000 | Hely | |
| 6,702,772 B1 | 3/2004 | Colditz | |
| 6,730,053 B1 | 5/2004 | Bodenschatz et al. | |
| 6,783,507 B1 | 8/2004 | Fisher | |
| 6,849,056 B1 | 2/2005 | Wiggins et al. | |
| 7,537,577 B2 | 5/2009 | Phelan et al. | |
| 7,713,223 B2 * | 5/2010 | Weber et al. | 602/21 |
| 7,824,352 B2 | 11/2010 | Jaccard | |
| 7,854,714 B1 | 12/2010 | Weber et al. | |
| 8,608,677 B2 * | 12/2013 | Motyer | A61F 5/0111 128/878 |
| 8,966,666 B2 * | 3/2015 | Faulconer | A63B 71/141 2/160 |
| 2009/0082708 A1 * | 3/2009 | Scott | A61F 5/0118 602/21 |
| 2011/0087145 A1 | 4/2011 | Farrow et al. | |

OTHER PUBLICATIONS

ProCare Wrist & Thumb Wrap, available at http://www.braceshop.com/productcart/pc/ProCare-Wrist-Thumb-Wrap-61p15512.htm.
http://www.braceshop.com/productcart/pc/DonJoy-Boomerang-Wrist-Brace-60p654.htm.
http://www.braceshop.com/productcart/pc/ProCare-Wrist-Thumb-Wrap-61p15512.htm.

* cited by examiner

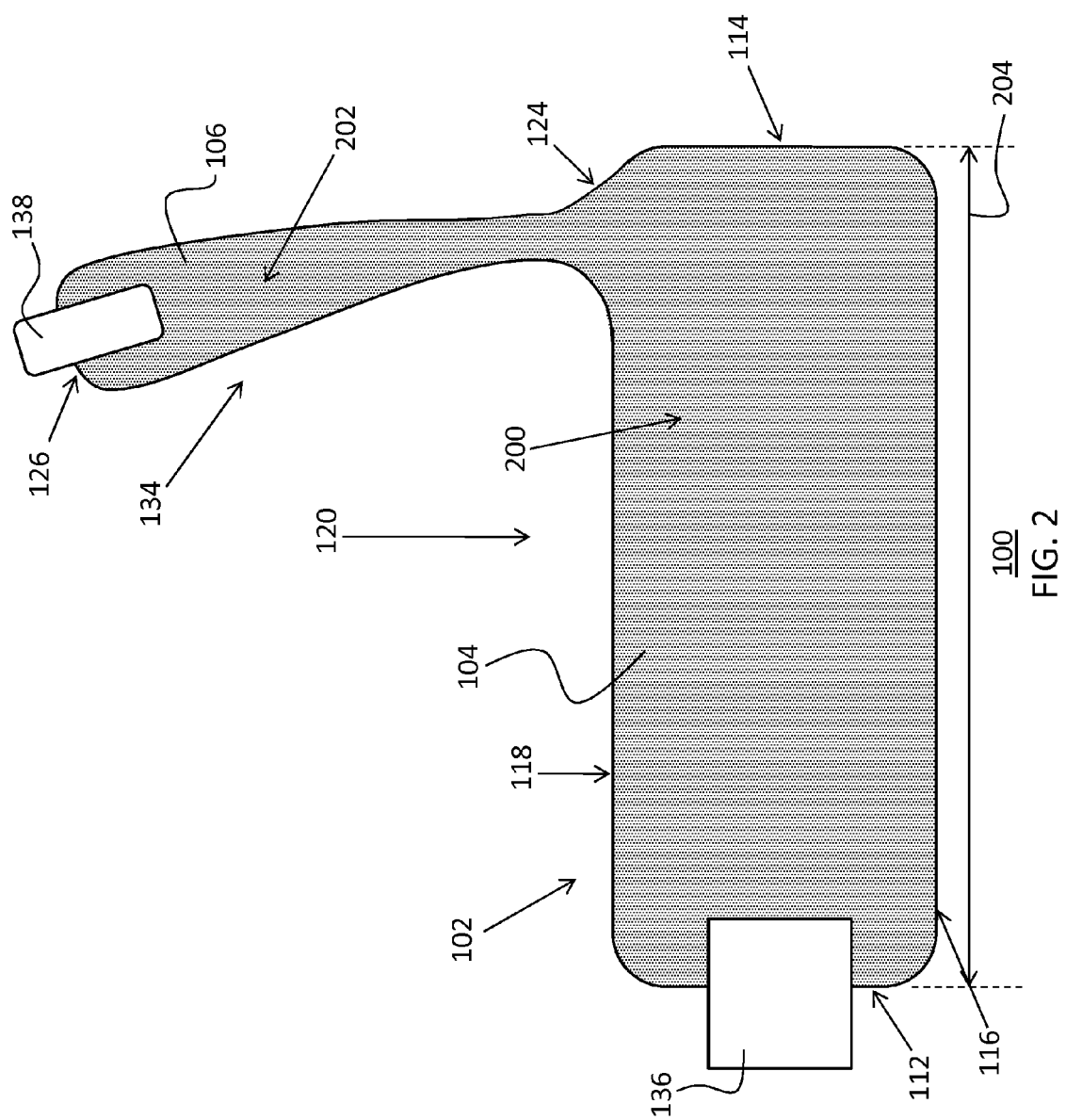

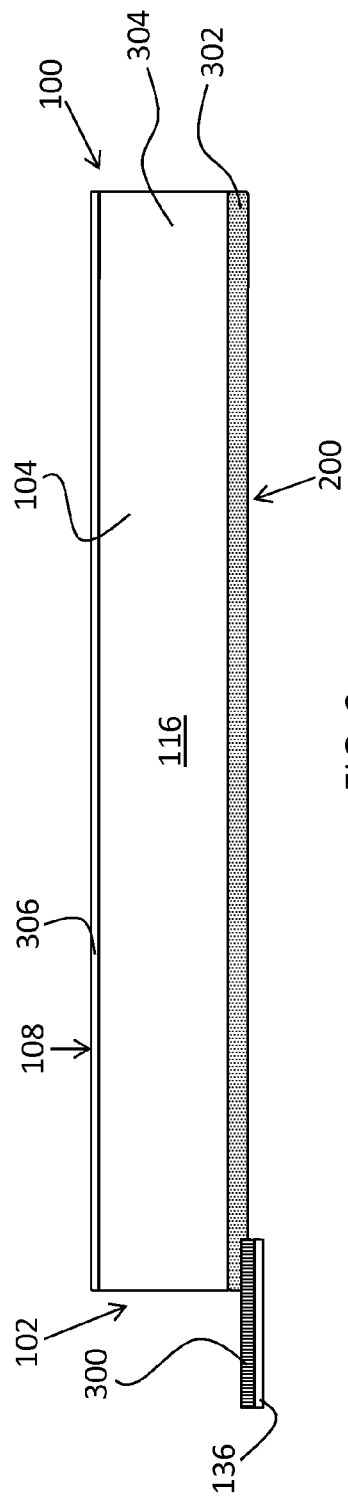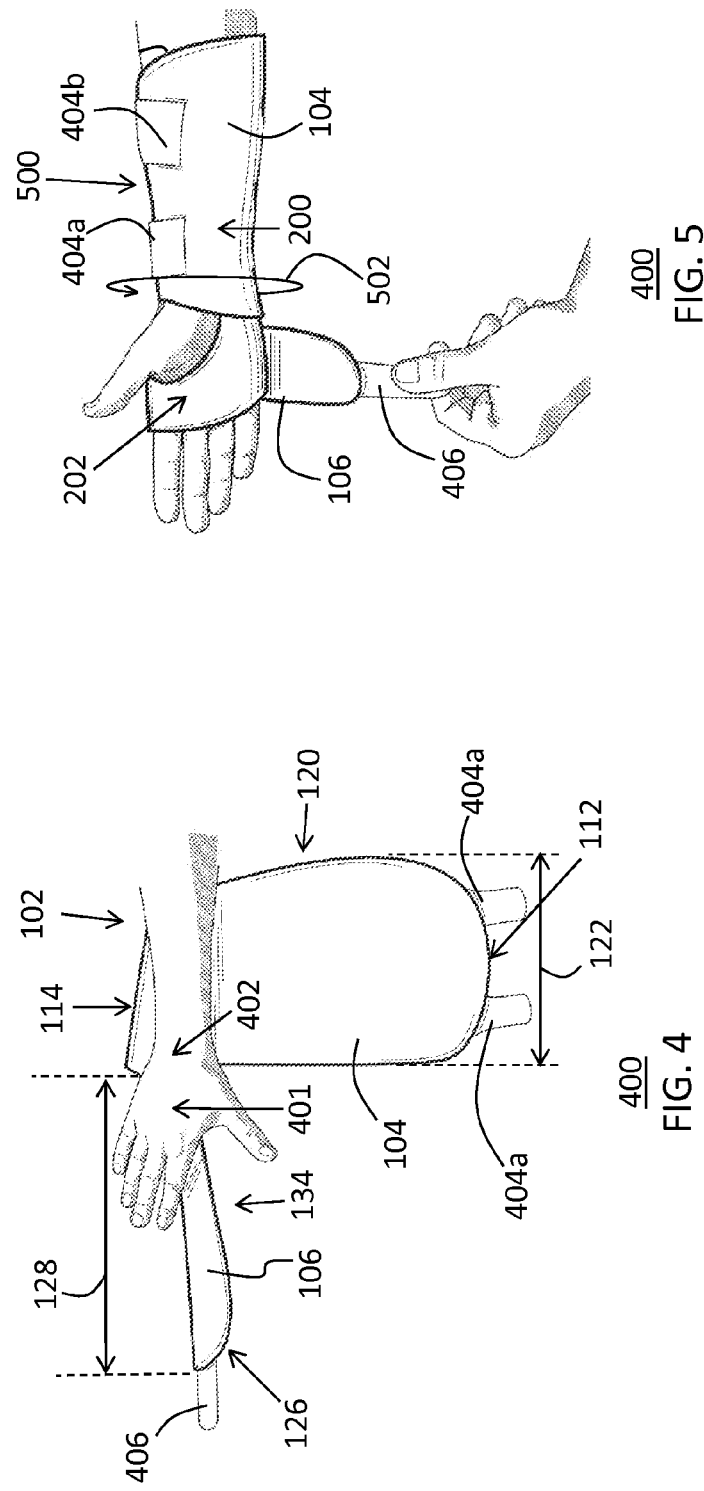

400

400

400

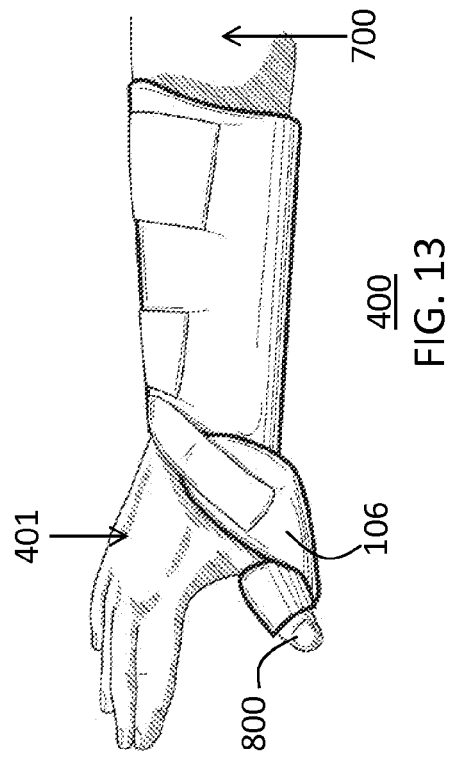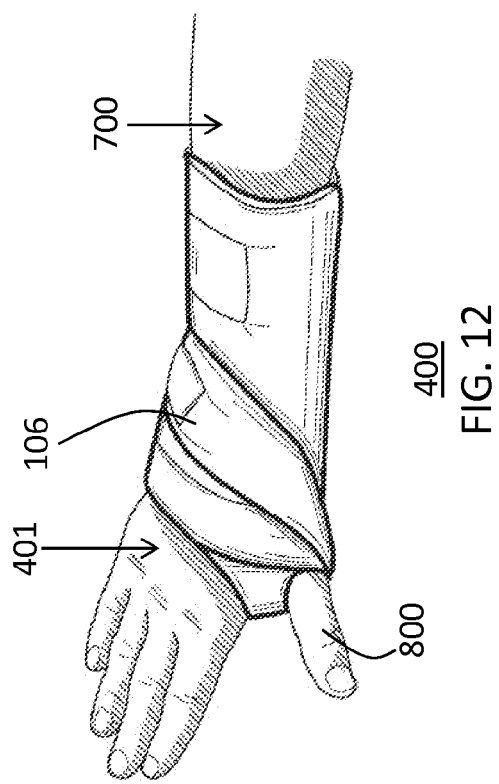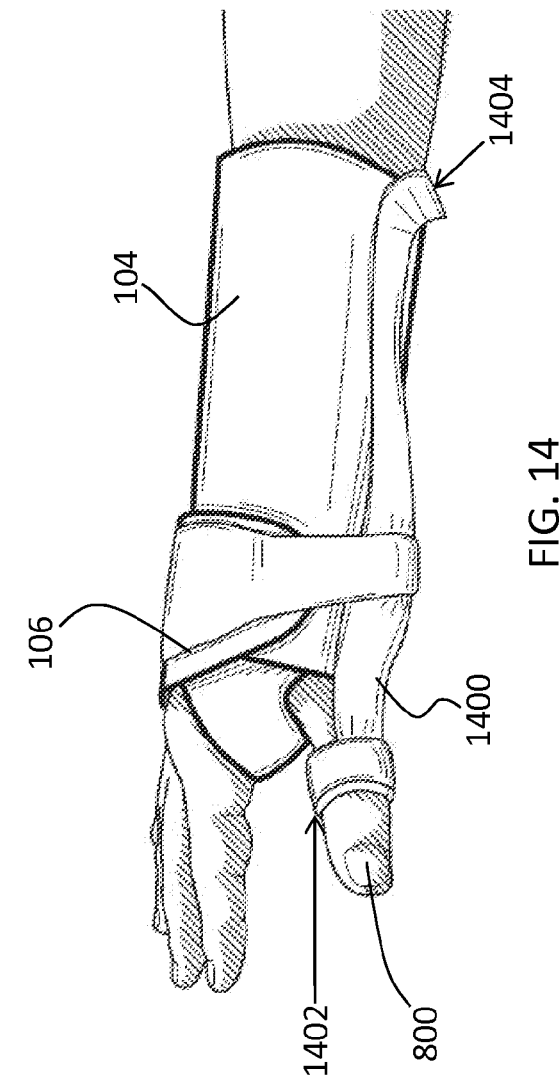
FIG. 12
FIG. 13
FIG. 14

FLEXIBLE HAND AND WRIST BRACE

FIELD OF THE INVENTION

The present invention relates generally to splints and braces, and more particularly relates to adjustable hand and wrist braces.

BACKGROUND OF THE INVENTION

It is a well-known fact that, for myriad reasons, people suffer injuries and pain to their hand(s) and/or wrist(s). Many of these injuries occur through accidents, over-extension of those muscles/joints/tendons (MJT) located within the hand or wrist, or simply through degeneration of those MJT. Regardless the source, most people treat or rehabilitate those injuries. To treat the pain and rehabilitate those injuries of the wrist and hand, many people employ the use of braces, splints, or casts. These braces, splints, and casts provide protection to the injured area, reduce pain and inflammation, help in scar management resulting from burns, provide MJT protection, improve joint motion, and much more.

Many apparatuses and methods for supporting, treating, and rehabilitating hand and wrist injuries have developed significantly over the years. Traditionally, an injured area of the hand or wrist is placed in a plaster or fiberglass mold wherein the hand or arm is set in place. These are typically known as "rigid braces." Casts are still utilized today, but they create many difficulties for a user. They are generally very time intensive to set-up, costly, difficult to remove, difficult to maintain, limited in configurations, and are generally uncomfortable for the user. Further, casts are difficult to maintain as they generally retain moisture from the showering or perspiration of the user. This moisture generates odors, which is undesirable for most users. Although there may be instances where rigid braces may be required to heal a bone fracture, they are still generally difficult to set-up, costly, and generally only support a specific injury on the hand or wrist.

Two other classes of braces include both soft and semi-rigid braces. Soft braces generally include a single piece of material that is shaped to conform to, or wrap around, the hand or wrist in order to generate pressure uniformly to all portions of the hand or wrist, rather than specifically focusing on the injured portion. Semi-rigid braces are generally a hybrid of soft and rigid braces, and typically include a single piece of material with straps and/or rigid splints to relieve pain, limit mobility of the effected area, and treat the specific injury. Those known soft and semi-rigid braces also suffer from many of the disadvantages described above for rigid braces. Specifically, those braces have limited functionality to relieve and treat pain for multiple injuries involving the hand and wrist.

For example, to treat sprains and perhaps even wrist fractures, some known soft and semi-rigid braces have straps (or gloves) that surround the wrist area of a user to substantially restrict movement. These braces restrict movement by applying significant amounts of pressure to the wrist. These braces would be inapplicable, and counter-productive, to treat a condition such as carpel tunnel syndrome, where immobilization of the wrist is required without the surface pressure that may irritate the median nerve. As such, those known braces are not capable of treating multiple conditions or injuries with a single brace. Consequently, hospitals or rehabilitation clinics, and individual users are required to purchase multiple braces dependent on the injury. This is extremely inconvenient and costly for those users and persons/entities involved in the medical community.

Furthermore, most soft or semi-rigid braces do not provide a user with the ability to simultaneously restrict movement of a MJT, but then allow that same brace to be configured (during the rehabilitation process) to progressively allow small increments of movement. Accordingly, these braces do not provide a single structure that allows a user to increase/reduce various degrees of motions, independently, such as: supination or pronation of the forearm, ulnar and radial deviation, and extension and flexion of the wrist. The inflexibility of a single brace to accommodate various injuries and different needs during rehabilitation process is problematic for many users.

Furthermore, to apply adequate support to the hand and wrist of a user, many hand and wrist braces require rigid material, i.e. splint, to be inserted within, or attached to, the brace. Besides contributing to the inflexibility of the brace to be configured to treat other injuries, these splints generally are more difficult to maintain, are more costly, and reduce the functionality of the brace should the splint mechanically fail. Moreover, many semi-rigid/rigid braces are also difficult to store and transport when not in use, as they are not able to be folded, or require time to disassemble, before transport. Similarly, many soft or semi-rigid braces that are formed into a glove-like structure are also difficult to transport, provide limited versatility in treating various injuries and conditions, and are difficult to comfortably accommodate users with various-sized wrists and hands.

Therefore, a need exists to overcome the problems with the prior art as discussed above.

SUMMARY OF THE INVENTION

The invention provides a flexible hand and wrist brace that overcomes the hereinafore-mentioned disadvantages of the heretofore-known devices and methods of this general type and that provides multiple configurations with a unitary body structure.

With the foregoing and other objects in view, there is provided, in accordance with the invention, a hand and wrist brace having a body including a first support member and a second support member. The first support member has an inner surface and an opposing outer surface, a left end, an opposing right end, and a first fastening element coupled to at least one of the left end and right end, a lower end and an opposing upper end, and a first position along a wrist support path with the left and right ends being uncoupled and a second position along the wrist support path with the left and right ends being coupled with the first fastening element to substantially encapsulate a portion of a user's wrist. The second support member has an inner surface and an opposing outer surface, a proximal end coupled to the first support member, a distal end, a length separating the proximal and distal ends, and a second fastening element coupled along the second support member length. The second support member also extends outwardly from the upper end of the first support member, has a first position along a secondary support path with the distal end uncoupled from the first support member, and has a second position along a secondary support path with the second fastening element that is removably-couplable to a plurality of locations on the outer surfaces of both the first support member and the second support member.

In accordance with another feature, an embodiment of the present invention includes a substantially elastic material separating the inner and outer surfaces of the first and second support members.

In accordance with a further feature of the present invention, the body is substantially stretchable.

In accordance with a further feature of the present invention, the body is free of any substantially rigid splints coupled thereto.

In accordance with yet another feature, an embodiment of the present invention includes the first support member further having a substantially planar orientation when in the first position along the wrist support path.

In accordance with another feature of the present invention, the first and second fastening elements are removably-couplable, when in their respective second positions, with a hook-and-loop attachment.

In accordance with a further feature of the present invention, the second support member length is sufficiently-sized to substantially surround at least 50% of the circumferential outer surface of the first support member when in the second position.

In accordance with a feature of the present invention, the second support member length is sufficiently-sized to substantially surround the circumferential outer surface of the first support member when in the second position at least once.

In accordance with another feature, an embodiment of the present invention includes the first support member further having a length separating the upper and lower ends, wherein the first support member length is less than the second support member length when the second support member is in the second position.

The disclosure also provides, in accordance with the invention, a hand and wrist, non-gloved, brace that has a body including a wrist support member and a second hand/wrist support member. The wrist support member has an inner surface and an outer surface, a left end, a right end, a lower end, and an upper end, a first fastening element coupled to at least one of the left end and right end, a first position along a wrist support path with the left and right ends being uncoupled and a second position along the wrist support path with the first fastening element coupled to the outer surface of the wrist support member to substantially encapsulate a portion of a user's wrist. The second hand/wrist support member has an inner surface and an outer surface, a proximal end coupled to the wrist support member, a distal end, and a length separating the proximal and distal ends. The second hand/wrist support member also extends outwardly from the upper end of the wrist support member, has a second fastening element coupled to the distal end of the second hand/wrist support member, has a first position along a secondary support path with distal end uncoupled to the second hand/wrist support member, and has a second position along a secondary support path with second fastening element removably-couplable to the outer surfaces of both the wrist support member and second hand/wrist support member.

In accordance with another feature, an embodiment of the present invention includes the second fastening element being removably-couplable to a plurality of locations on the outer surfaces of the wrist support member and the second hand/wrist support member with a hook-and-loop attachment.

In accordance with a feature of the present invention, the second hand/wrist support member length is at least six inches when in the first position along the secondary support path.

In accordance with the present invention, a method for bracing and supporting a hand and wrist of a user, with the including the steps of first providing a body including a wrist support member having an inner surface, an outer surface, a left end, a right end, a lower end, and an upper end, and a first position along a wrist support path with the left and right ends being uncoupled and a second position along the wrist support path with the left and right ends being coupled together. The body also includes a second hand/wrist support member that has an inner surface and an outer surface, a proximal end coupled to the wrist support member, a distal end, and a length separating the proximal and distal ends, the length being sufficiently-sized to substantially surround at least 50% of the circumferential outer surface of the wrist support member when in the second position. The second hand/wrist support member also extends outwardly from the upper end of the wrist support member, and has a first position along a secondary support path with the distal end uncoupled to the wrist support member and a second position along the secondary support path with the second hand/wrist support being removably-couplable to the outer surfaces of both the wrist support member and the second hand/wrist support member. The method further includes the steps of placing the wrist support member and second hand/wrist support member in the first position, positioning a portion the second hand/wrist support member between a web portion defined by an index finger and a thumb of a user's hand, coupling the left and right ends of the wrist support member to substantially encapsulate a user's wrist, and coupling the second hand/wrist support member to the outer surface of the second hand/wrist support member.

Although the invention is illustrated and described herein as embodied in a flexible hand and wrist brace, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction from the left end toward the right end of the first support member.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 2 is a plan view of the hand and wrist brace of FIG. 1, showing an outer surface of both the first and second support members in accordance with present invention;

FIG. 3 is an elevational close-up rear view from the lower end of the first support member of FIG. 1 having a first fastener coupled to the first support member with a hook-and-loop attachment in accordance with an exemplary embodiment of the present invention;

FIG. 4 is a top perspective view of the dorsal side of a user's hand being placed over a hand-and-wrist brace while the first and second support members are in first positions along a wrist support path and a secondary support path, respectively, according to an exemplary embodiment of the present invention;

FIG. 5 is a perspective view of the volar side of the user's hand, with the brace of FIG. 4 attached thereto and the second support member being in a second position along the wrist support path according to an exemplary embodiment of the present invention;

FIG. 12 is a perspective, downward-looking, view of the hand-and-wrist brace of FIG. 4 in another supporting configuration in accordance with the present invention;

FIG. 13 is an elevational view, from the radial side of the user's hand, of another exemplary embodiment of the hand-and-wrist brace of FIG. 4 in another supporting configuration in accordance with the present invention;

FIG. 14 is an elevational view, from the radial side of the user's hand, of the hand-and-wrist brace of FIG. 4 in another supporting configuration that includes a thumb extension attachment in accordance with the present invention.

DETAILED DESCRIPTION

Figure 1:
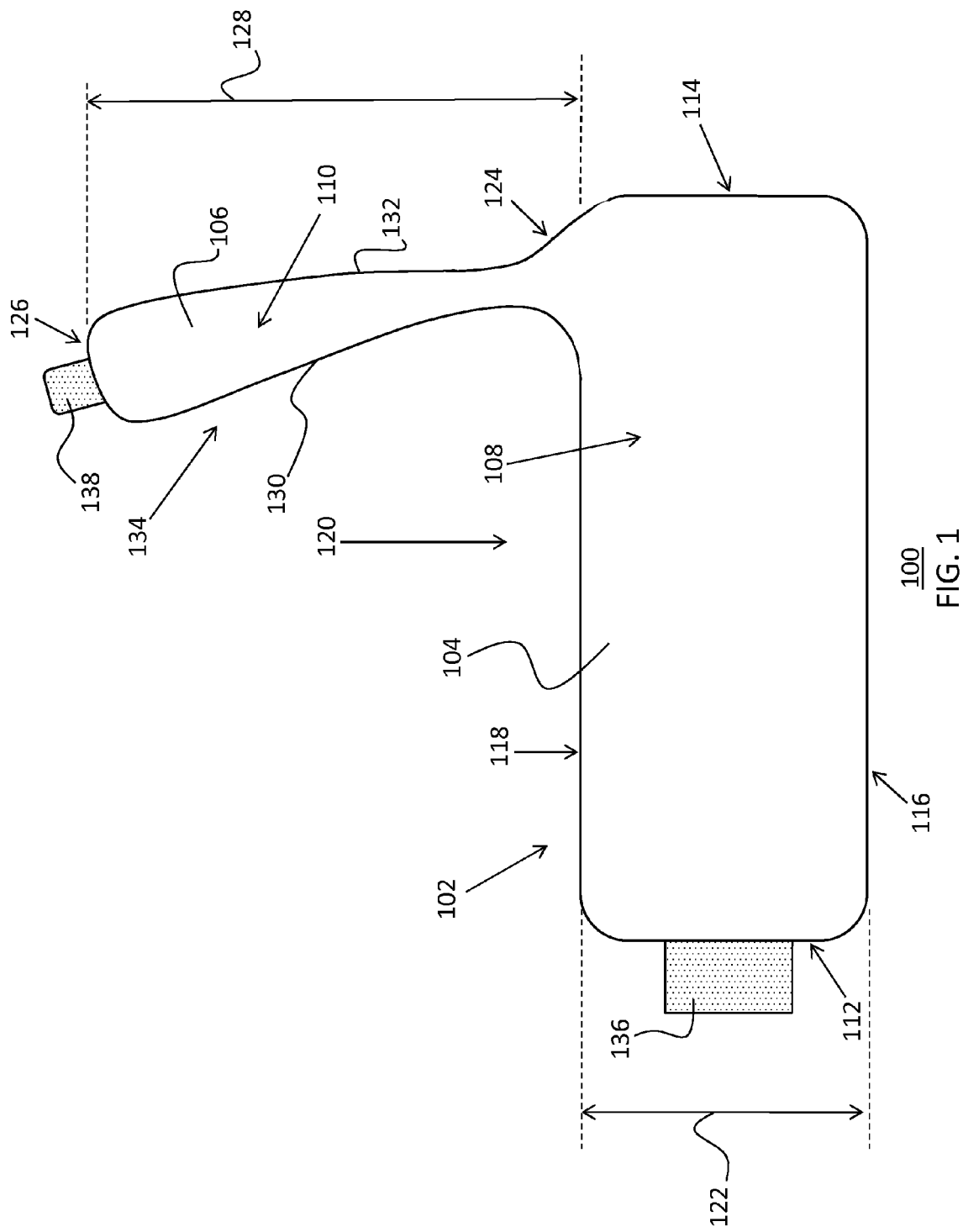
FIG. 1 is a plan view of a hand and wrist brace showing an inner surface of both the first and second support members in accordance with present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient hand and wrist brace that may be configured to support, and relieve pain in, the hand and wrist areas of a user. Embodiments of the present invention allow a user to manipulate the brace in at least 18 different configurations to treat and support a myriad of hand and wrist injuries and/or conditions. In addition, further embodiments provide a brace that easily and effectively supports the hand and wrist areas of the user with very little components and with very little ease. Additional embodiments also provide a user with a non-gloved brace capable of accommodating multiple users having various-sized hands.

Referring now to FIGS. 1 and 2, one embodiment of the present invention is shown in top and bottom plan views, respectively. FIGS. 1 and 2 show several advantageous features of the present invention, but, as will be described below, the invention can be provided in several shapes, sizes, combinations of features and components, and varying numbers and functions of the components. The first example of a hand and wrist brace 100, as shown in FIGS. 1 and 2, includes a body 102 with a first support member 104, also referred to herein as a wrist support member, and a second support member 106, also referred to herein as a second hand/wrist support member. Although the present invention is referred to as a brace 100, it shall not be so limited, as those skilled in the art can appreciate that the present invention performs similar functions of a brace, splint, bandage, and/or cast.

Both the first and second support members 104, 106 can be seen having inner surfaces 108, 110 and outer surfaces 200, 202 (shown in FIG. 2), respectively. FIG. 2 illustrates the outer surfaces 200, 202 from a view-point looking underneath the support members 104, 106 as they are positioned in FIG. 1. In one embodiment, the body 102 is unitary, in that the first and second support members 104, 106 are formed from the same piece of material. As a corollary, the inner surfaces 108, 110 and outer surfaces 200, 202 would also be one and the same, respectively. This advantageously allows the brace 100 to be cut or formed in a single step, without the need for other components (such as stays), thereby decreasing the costs and time associated with manufacturing the brace 100. The unitary body 102 and/or material used to form the body also allows a therapist (or other user/owner) to modify or shape the body 102 for a more customized fit for the user. The quick and easy customization of the body 102 provides a user with a more comfortable and effective hand/wrist brace 100. The unitary shape of the brace 100 further provides a user with the ability to easily transport and carry the brace 100 when not in use. In other embodiments, the first and second support members are separate and are coupled together with adhesives, are sewn together, or are attached with another coupling method.

In one embodiment, both inner surfaces 108, 110 and outer surfaces 200, 202 of the first and second support members 104, 106, respectively, are at least partially separated by a substantially elastic material. The elastic material generally allows the body 102 to deform in order to accommodate and provide pressure on various-sized wrists/hands of a user. In one embodiment, the material may be polymer based, such as neoprene, EPDM, natural rubber, breathoprene, or silicone. The material generally may not have any plastic deformation and has a percent elongation ranging from approximately 150%-250%. In other embodiments, the material may be a composite, a stretchable fabric, or other material that allows elastic strain with very little, if any, plastic deformation when a user's hand applies a tensional force on the body 102. Further, the percent elongation may be less than or greater than the aforementioned range, but capable and sufficient enough to apply a sufficient pressure upon a user's wrist and/or hand to support the same. In other embodiments, just the first support member 104 is generally made from a substantially elastic material, or none of the support members 104, 106 may be made from a substantially elastic material.

In further embodiments, the body 102 may be substantially flexible to allow it to be bent or pliable for easy storing and durability. Said another way, the brace 100 may not require any rigid objects, such as splints or stays, to support and treat a user's injuries, which is generally required with many prior-art braces. The brace 100 may be folded when not utilized and easily unfolded when desired to be used to support a myriad of hand and wrist conditions, without the need for additional components.

Still referring to FIGS. 1 and 2, the first support member 104 has a left end 112 and a right end 114, opposite to the left end 112. Further, the first support member 104 also has a lower end 116 and an upper end 118, opposite to the lower end 116. The first support member 104 provides support, by applying pressure to the wrist and forearm of a user. The first support member 104 may also provide support and pressure to the palmar surface just after the wrist crease of a user.

When the brace 100 is not being utilized, it can be said to have a first position 120 along a wrist support path with the left and right ends 112, 114 being uncoupled to each other, as shown in FIGS. 1 and 2. The first position 120 allows a user to place either the volar or dorsal portion of their hand and/or wrist on, or above, the inner surfaces 108, 110 of the first and second support members 104, 106. The first support member 104 also has a second position 500 (shown in FIG. 5) along the wrist support path with the left and right ends 112, 114 being coupled together to substantially encapsulate a user's wrist. The term "encapsulate" is defined herein as having some portion of a referenced structure or object lying in between another structure or object.

In one embodiment, the first support member 104 may define a generally rectangular shape when in the first position 120 along the wrist support path. Furthermore, the first support member 104 may also be in substantially planar orientation when also in the first position 120 along the wrist support path. The first support member 104 is exemplified with the above characteristics in FIGS. 1 and 2. The generally rectangular shape of the support member 104 assures that it completely surrounds, and generates sufficient pressure with, the user's wrist. In other embodiments, the first support member 104 may be curvilinear in nature, i.e. non-planar, when viewed from the side of the brace 100 and when in the first position 120. Furthermore, the first support member 104 may have one or more apertures located thereon that may expose the user's wrist. Any apertures located on the first support member 104, would still permit the two ends 112, 114 to couple together, although not necessarily directly, i.e., through the member 104, and encapsulate and apply surface tension to the user's wrist. As the brace 100 is not shaped initially in a glove-like structure, the brace 100 can advantageously adapt to users of different ages and sizes, comfortably and effectively, which is not generally capable with those prior-art braces utilizing a glove-like structure. Those glove-like structures are those shaped like a standard glove, specifically having preformed apertures in the brace to receive the fingers/thumb of a user.

The first support member 104 has a length 122 separating the lower and upper ends 116, 118. The ends 116, 118 of the first support member 104 are generally shown in FIGS. 1 and 2 as being equidistant to one another. In other embodiments, the ends 116, 118 may have portions that are disproportionate in length 122 to one another, such that the length 122 would be said to be the shortest distance between two opposite ends 116, 118. FIG. 2 illustrates the left and right ends 112, 114 also being separated by a width 204. In one embodiment, the length 122 ranges approximately from 5-8 inches and the width 204 ranges approximately from 10-12 inches. In other embodiments, the length 122 and width 204 may vary, but generally define dimensions of the first support member 104 sufficient to encapsulate and apply pressure to a user's wrist when the support member 104 is in the second position 500 (shown in FIG. 5).

With reference back to FIG. 1, the second support member 106 can be seen having a proximal end 124 coupled to the first support member 104, a distal end 126 opposite the proximal end 124, and a length 128 separating the proximal and distal ends 124, 126. The second support member 106 extends outwardly from the upper end 118 of the first support member 104. As the brace 100 is designed to function with both the left and right hand of a user, in one embodiment, for the right hand, the second support member 106 may extend outwardly within close proximity to the right end 114. In other embodiments, for the left hand, the second support member 106 may extend outwardly within close proximity to the left end 112. In one embodiment, the second support member 106 extends at an acute angle, i.e. 70°, with respect to the upper end 118. In other embodiments, the second support member 106 may extend outwardly at an angle that is substantially perpendicular or obtuse with respect to the upper end 118. The left and right edges 130, 132 of the second support member 106 may be generally linear or curvilinear in shape. The second support member 106 should be located, and have at least one portion with a width separating the left and right edges 130, 132, sufficient to fit between the index finger and thumb of a user's hand.

The second support member 106 has a first position 134 along a secondary support path with the distal end 126 uncoupled to the first support member 104. The second support member 106 also has a second position 600 (shown in FIG. 6) along the secondary support path with the distal end 126 being removably-couplable to a plurality of locations on the outer surfaces 200, 202 (shown in FIG. 2) of both the first and second support members 104, 106. The secondary support path generally defines the range of motion from a point where the second support member 106 is free and uncoupled, to a point where it is advantageously coupled to uniquely create at least approximately 18 configurations. Each of these configurations supports different injuries and/or conditions associated with the hand or wrist. These configurations also allow the user to progressively vary the ranges of motion in the forearm, wrist, and even fingers, beneficially, with just one brace. As such, one brace 100 may treat multiple injuries that previously required multiple separate and distinct prior-art braces and/or splints.

Still referring to FIGS. 1 and 2, the left and right ends 112, 114 of the first support member 104 are coupled together with a first fastening element 136. Further, the second support member 106 is either coupled to itself or to the first support member 104 with a second fastening element 138. In one embodiment, the first fastening element 136 is attached at the left end 112, but in other embodiments, it may be attached to right end 114 or anywhere along the width 204 of the first support member 104. The second fastening element 138 may be fastened along the second support member length 128. As shown in FIGS. 1 and 2, the second fastening element 138 may be fastened at the distal end 126 or may be fastened just below the distal end 126 to reduce excess material from being exposed and freely hanging when the second support member 106 is in the second position 600 (shown in FIG. 6). In one embodiment, the first and second fastening elements 136, 138 are removably-couplable to either (or both of) the first and second support members 104, 106, when in their second positions 500, 600 (shown in FIGS. 5 and 6), with a hook-and-loop attachment.

In one embodiment, the entire outer surfaces 200, 202 of the support members 104, 106 are made of a fabric loop material. In other embodiments, some portions of the outer surfaces 200, 202 may not have the fabric loop material or the outer surfaces 200, 202 may be the hook material, and the first and second fastening elements 136, 138 may have the loop material. In further embodiments, the first and second fastening elements 136, 138 are removably-couplable to either (or both of) the first and second support members 104, 106 with a plurality of snaps, pins, or other coupling methods capable of providing the second support member 106 multiple attachment locations.

With reference now to FIG. 3, the brace 100 is shown in a close-up elevational, rear view from the lower end 116 of the first support member 104. The first fastening element 136 is shown coupled to the outer surface 200 of the first support member 104 using a hook-and-loop attachment, such as VELCRO. The first fastening element 136 is exemplified with the hook material 300 and the outer surface 200 has the loop material 302. As previously discussed, the outer surfaces 200, 202 and inner surfaces 108, 110 of both support members 104, 106, respectively, are at least partially separated by a substantially flexible material 304. In further embodiments, the one or more portions of the inner surfaces 108, 110 of both support members 104, 106, respectively, may also have a fabric 306 attached thereto. The fabric 306 generates a comfortable contact surface with the user's hand and/or wrist, when the support members 104, 106 are in their respective second positions 500, 600 (shown in FIGS. 5 and 6).

Another advantageous feature of the present invention includes one or more of the fastening elements 136, 138 being completely removable from the first or second support members 104, 106. When the brace 100 utilizes a hook-and-loop attachment, the fastening elements 136, 138 may be repositioned anywhere along the outer surfaces 200, 202. This beneficially permits a user to obtain a more precise coupling contact when the support members 104, 106 are in their respective second positions 500, 600 (shown in FIGS. 5 and 6). It further permits the user to adjust the brace 100 to generate maximum comfort while the brace 100 is being utilized and to facilitate more or less range of motion in the wrist, hand, or forearm. Although FIGS. 1-3 have illustrated two fastening elements 136, 138 coupled to the body 102, the brace 100 may employ more than two fastening elements 136, 138 to couple the support members 104, 106 when they are in their respective second positions 500, 600 (shown in FIGS. 5 and 6).

Figure 6:
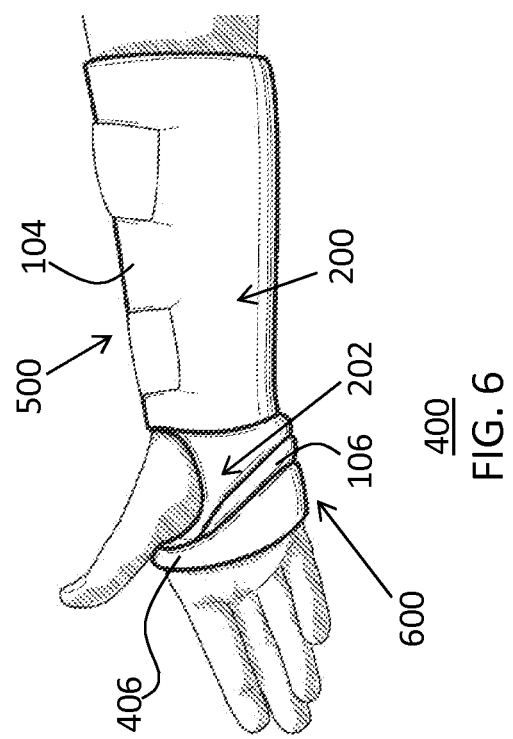
FIG. 6 is an elevational view, from of the volar side of the user's hand, with the brace of FIG. 4 attached thereto and both the first and second support members being in second positions along the wrist support path and secondary support path, respectively, according to an exemplary embodiment of the present invention.

With reference now to FIGS. 4-6, one embodiment of the brace 400 is shown with the first and second support members 104, 106 transitioning between their respective first positions 120, 134 and second positions 500, 600. FIGS. 4-6 also illustrate one of the myriad configurations available for the brace 400. The brace 400 is able to accomplish these configurations, in part, because of the length 128 and elasticity of the second support member 106. In one embodiment, the second support member length 128 length is sufficiently sized to substantially surround at least 50% of the circumferential outer surface 200 of the first support member 104 when in the second position 500. The circumference outer surface is the surface 200 that circumferentially surrounds the wrist of the user and does not include any portions of the first support member 104 that may overlap with one another (when in the second position 500). In embodiments where the second support member 106 is made with a substantially elastic material, the length 128 will vary depending on whether it is in its static or dynamic state. Should the material of the second support member 106 be substantially elastic, then the length 128, in accordance with one embodiment of the present invention, is sufficient to substantially surround at least 50% of the outer surface 200 of the first support member 104 when it is in the second position 500 and will at least be the length 128 of the support member 106 when in its dynamic state. This advantageously permits a user to support different portions of the hand and wrist, depending on the injury or condition the user is trying to alleviate or rehabilitate.

In other embodiments, the length 128 would be sufficiently sized to substantially surround the circumferential outer surface 200 of the first support member 104, at least once, when it is in the second position 500. Said another way, the second support member 106 may have a length 128 sufficient to cover the circumference of the first support member 104 when in its second position 500 along the wrist support path. Again, the length 128 of the second support member 106 will at least be the length 128 of the support member 106 when in its dynamic state, should the material be substantially elastic. In yet further embodiments, the second support member length 128 is at least the length 122 of the first support member 104. Alternatively stated, the first support member length 122 may be less than the second support member length 128 when the second support member 106 is in the second position 600. This permits the second support member 106 to couple to multiple locations on the outer surface 200 of the first support member 104 and also on the outer surface 202 of the second support member 106.

In one embodiment, in order to set-up the brace 400 in a supporting configuration for the right hand, the user first places the body 102 with the inner surfaces 108, 110 of the first and second support members 104, 106, respectively, facing upwardly toward the volar hand 401 of the user. As shown in FIG. 4, the user places a portion of the second support member 106 between the index and thumb. The user then couples the left and right ends 112, 114 of the first support member 104 to substantially encapsulate the circumference of user's wrist 402 when in the second position 500 along the wrist support path. The user's wrist 402 generally extends from the wrist crease 900 to the upper forearm 902 (shown in FIG. 9), but may extend just beyond these boundaries. When in the second position 500 the first support member 104 can also be seen substantially encapsulating the lower-third forearm of the user. The first support member 104 is also shown with two fasteners 404a-b located on the left end 112 used to couple the ends 112, 114 together when in the second position 500. As previously mentioned, the fasteners 404a-b may be located on the right end 114, or other portions of the first support member 104. There may also be less, or greater than, the two fasteners 404a-b.

After the first support member 104 is in the second position 500, the user may then take the second support member 106 and move it from the first position 134 along the secondary support path to the second position 600. The first support member 104 is operable to be placed in multiple positions capable of supporting various portions of the hand, wrist, and forearm. As such, in one embodiment, the second support member 106 is removably-couplable to a plurality of locations on the outer surfaces 200, 202 of both the first support member 104 and the second support member 106 with a hook-and-loop attachment. As previously discussed, the distal end 126 of the second support member 106 may be couplable to a plurality of predetermined locations on the outer surfaces 200, 202, or may be couplable to all locations on the outer surfaces 200, 202. As shown in FIG. 6, the distal end is coupled to itself after first wrapping around the circumference of the hand. To increase the pressure to the wrist 402 or hand 401, the user may continue to stretch and pull the first or second support member 104, 106. As such, the pressure on the hand 401 or wrist 402 is generally proportional to the second support length 128 or second support width 204 (shown in FIG. 2), when varying from the static state to the dynamic state.

The second support member 106 may have one fastening element 406 attached thereto that facilitates coupling the first support member 104, when in the second position 600. In additional embodiments, the second support member length 128 is at least six inches when in the first position 134 along the secondary support path. This provides a user with the ability to at least surround a substantial circumferential (represented with an arrow 502) portion of a user's wrist 402 or hand 401, thereby still providing multiple support positions to treat multiple injuries. To remove the brace 400, the user uncouples the fastening elements 404a-b, 406 from any outer surfaces 200, 202 where they may be coupled.

As shown in FIGS. 4-6, the second support member 106 wraps around the ulnar portion of the hand and attaches to the radial portion of the hand 401. As can be appreciated, should the second support member be substantially elastic, the distal end 126 of the second support member 106 may further extend and coupled to a position just beyond the radial portion, approximately to the top of the hand. The configuration of the brace 400 shown in FIG. 6 provides orthopedic support for wrist fractures and reduces the effects of arthritis. Further, this configuration provides slow-stretch supination and radial deviation assistance for medical neurological conditions such as strokes, brain injuries, and spinal cord injuries.

In other embodiments, the second support member 106 may wrap around the ulnar styloid and couple to the first support member 104 (when in the second position 500) around the wrist crease/radial styloid of the user. This configuration comfortably and effectively relieves the effects causes by arthritis and carpal tunnel syndrome, as it does not exert too much surface pressure on the median nerve. The second support member 106 may also wrap around the ulnar styloid and the user's wrist to couple to the mid to lower dorsal forearm (towards the ulnar side). This configuration provides supination assist, also relieving the effects of various neurological and orthopedic conditions.

Figure 7:
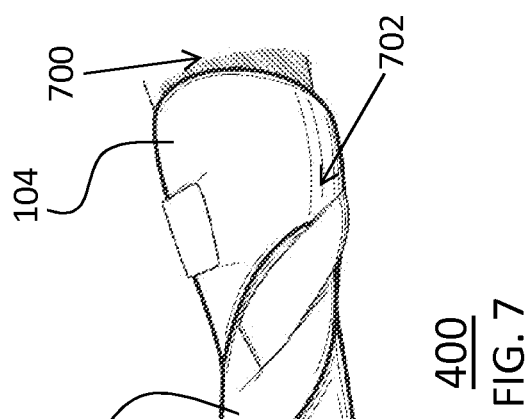
FIG. 7 is an elevational view, from the ulnar side of the user's hand, of the hand-and-wrist brace of FIG. 4 in another supporting configuration in accordance with the present invention.

With reference to FIG. 7, another embodiment of the brace 400 is illustrated. Specifically, the second support member 106 is shown wrapping around the base of the thumb and then traversing the mid to lower-third of the volar forearm 700 (towards the ulnar side) and then coupling at the side 702 of the mid forearm 700. In such a configuration, the brace 400 also relieves numerous neurological and orthopedic conditions described above. This and other configurations also provide a user with multiple placement positions for the second support member 106 that relieve pain and/or support an injury, that may be specific to each user.

Figure 8:
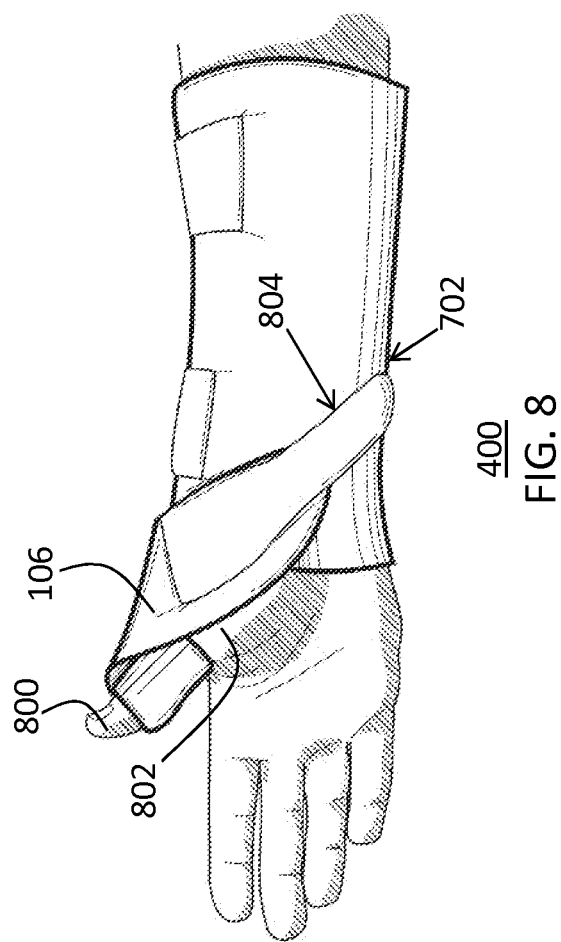
FIG. 8 is an elevational view, from the volar side of the user's hand, of the hand-and-wrist brace of FIG. 4 in another supporting configuration in accordance with the present invention.

There are a plethora of various configurations of the brace 400 that can be adjusted and fitted to treat various injuries. An embodiment of a brace 400 in another configuration is shown in FIG. 8. More particularly, the second support member 106 can be seen completely wrapping around the thumb 800 and traversing the radial portion of the thenar 802 and the coupling to the mid-portion of the volar wrist 804/ulnar side 702 of the forearm 700. This configuration relieves orthopedic conditions such as arthritis, De Quervain syndrome, tendonitis, and others.

Figure 10:
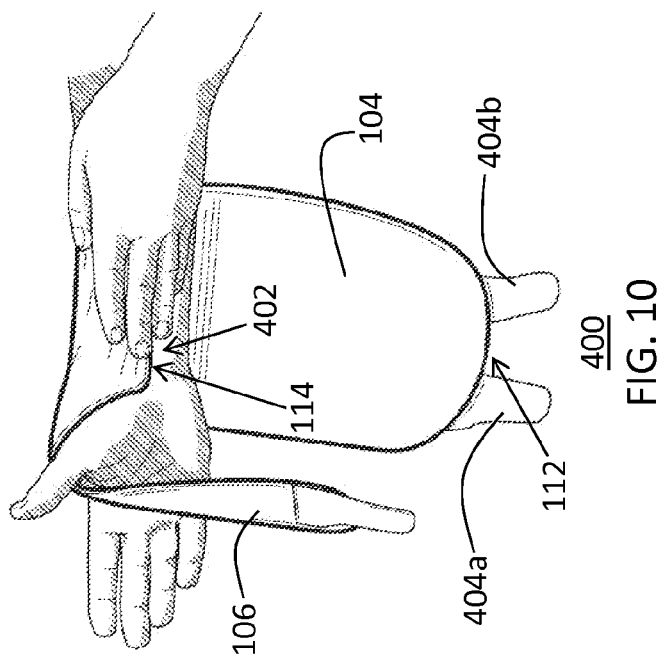
FIG. 10 is an elevational view, from the volar side of a user's hand, with the brace of FIG. 4 in the process of being attached to the user's hand-and-wrist area according to an exemplary embodiment of the present invention.
Figure 9:
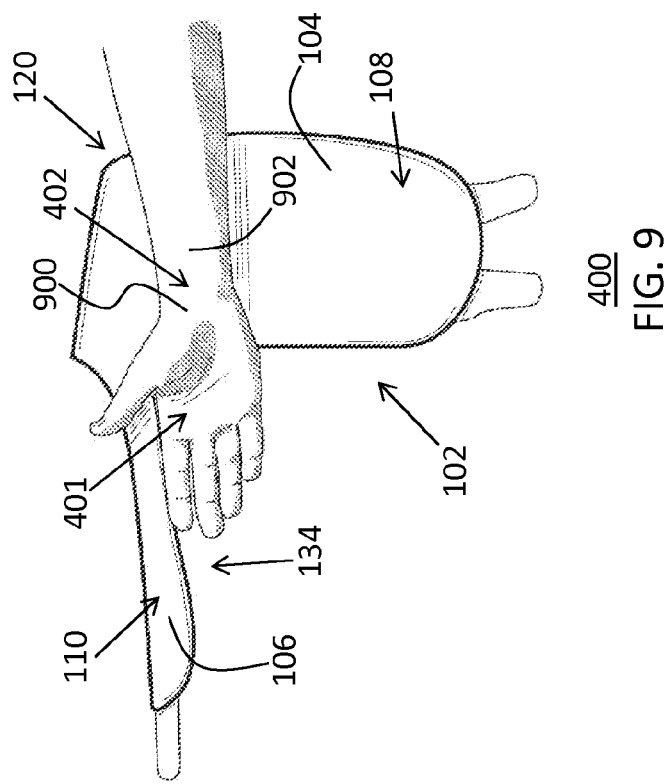
FIG. 9 is a top perspective view of the volar side of a user's hand being placed over the hand-and-wrist brace of FIG. 4 while the first and second support members are in first positions along a wrist support path and secondary support path, respectively, according to another exemplary embodiment of the present invention.

Referring now to FIG. 9, another embodiment is shown of the brace 400 in another configuration. In order to set up the brace 400 in another set of supporting configurations with the dorsal side of the user's hand 401 and/or wrist 402, the user first places the body 102 with the inner surfaces 108, 110 of the first and second support members 104, 106, respectively, facing upwardly toward the dorsal side of the hand 401 of the user. Both the first and second support members 104, 106 are shown in their first positions 120, 134 along the wrist support path and secondary support path, respectively. As shown in FIG. 9, the user places a portion of the second support member 106 between the index and thumb of the hand 401. FIG. 10 illustrates the user placing the right end 114 of the first support member 104 around the radial portions of the wrist 402 and lower-third/mid forearm. As described above, the left end 112 is coupled with another portion of the first support member 104 to substantially encapsulate the user's wrist 402. This may be accomplished with the fastening elements 404*a-b*.

Figure 11:
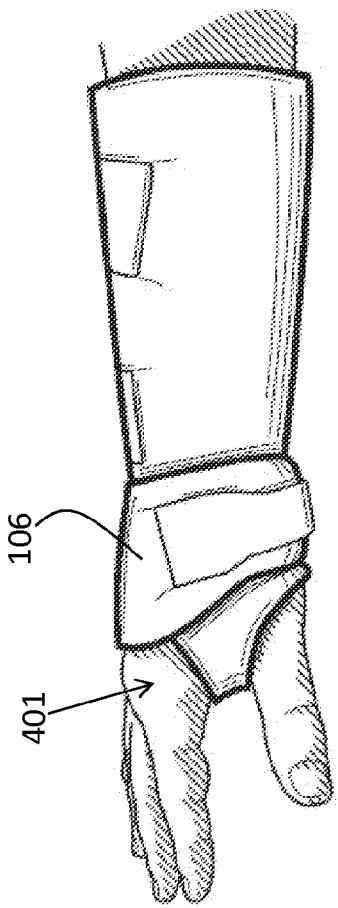
FIG. 11 is an elevational view, from the radial side of the user's hand, with the brace of FIG. 4 attached thereto and both the first and second support members being in second positions along the wrist support path and secondary support path, respectively, according to an exemplary embodiment of the present invention.

FIG. 11 illustrates one result of the above hand 401 and wrist 402 (not shown) orientations shown in FIGS. 9 and 10. The second support member 106 is wrapped around the ulnar hand 401 and coupled to the radial portion of the wrist 402 (not shown). This configuration also supports numerous neurological and orthopedic conditions. FIGS. 12 and 13 illustrate two other configurations of the brace 400 after the dorsal hand 401 is placed in the orientation shown in FIG. 9. FIG. 12 shows the second support member 106 around the base of the thumb 800, traversing the dorsal forearm towards the ulnar side with mild tensional force applied to the second support member 106. This configuration supports supination of the forearm 700 and varying the range of motion in the hand 401. FIG. 13 shows the second support member 106 all around the base of the thumb 800, and coupling the support member 106 to the dorsal wrist 402 (not shown).

FIG. 14 illustrates another feature of the present invention. A thumb extension attachment 1400 is shown with a distal end 1402 coupled onto the thumb 800 of a user and a proximal end 1404 coupled to the first support member 104. The ends 1402, 1404 may have an inner and outer surface that have the same hook-and-loop attachment as the first and second support members 104, 106. In one embodiment, the distal end 1402 of the attachment 1400 wraps around the thumb 800 and then traverses the radial wrist and forearm of the user where it is coupled to the first support member 104. In further embodiments, the second support member 106 may couple to or traverse the attachment 1400. The thumb attachment 1400 provides an embodiment that assists in either abnormal tone or sub-acute extensor tendon repair, among others.

Figure 15:
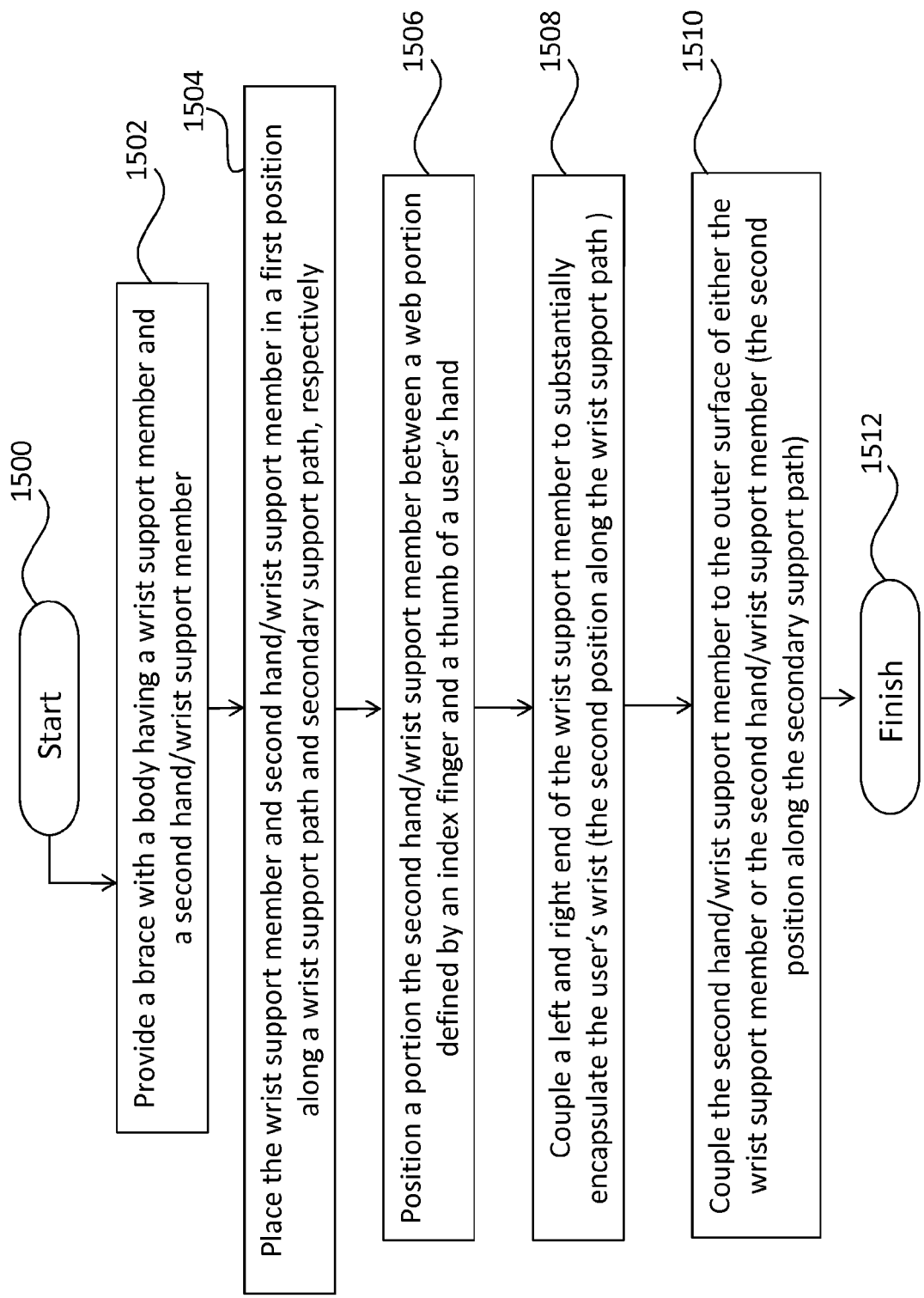
FIG. 15 is a process flow diagram representing a method of bracing and supporting a hand and wrist of a user in accordance with the present invention.

FIG. 15 illustrates a process flow diagram of the above described method of bracing and supporting a hand and wrist of a user. The process starts at step 1500 and immediate proceeds to step 1502, where the user is provided with a brace that has the aforementioned body, having a wrist support member and a hand/wrist support member. The next step 1504 includes placing the wrist support member and second hand/wrist support member in the first position. The first position along the wrist support path for the wrist support member includes the left and right ends being uncoupled. The first position along the secondary support path for the second hand/wrist support member includes the distal end uncoupled to the wrist support member.

The next step 1506 includes positioning a portion the second hand/wrist support member between a web portion defined by an index finger and a thumb of a user's hand. Subsequently, in the following step 1508, the user couples the left and right ends of the wrist support member to substantially encapsulate the user's wrist. The next step 1510 includes the user coupling the second hand/wrist support member to the outer surface of either the wrist support member or the second hand/wrist support member. This advantageously allows the user to couple the second hand/wrist support member to multiple locations on the wrist support member or itself. The process concludes at step 1512.

A hand and wrist brace, and method of application, has been disclosed that uniquely supports a myriad of hand and wrist injuries with a low-cost and easy to use structure. The brace advantageously allows the user to connect a secondary support member of a brace to multiple locations around the wrist support member or the secondary support members. The above disclosed brace permits at least approximately 18 configurations, but medical providers or users may experiment and coupled the brace in various configurations that is beneficially tailored for a specific user.

What is claimed is:

1. A hand and wrist brace comprising:
A body free from any rigid splints coupled thereto, the body including:
a first support member having:
an inner surface and an opposing outer surface;
a left end, an opposing right end, and a first fastening element coupled to at least one of the left end and right end;
a lower end and an opposing upper end; and
a first position along a wrist support path with the left and right ends being uncoupled and a second position along the wrist support path with the left and right ends being coupled with the first fastening element to substantially encapsulate a portion of a user's wrist; and
a second support member:
having an inner surface and an opposing outer surface;
made of a substantially elastic material, the substantially elastic material configured to provide pressure to an entire portion of a user's wrist;
having a proximal end directly coupled to the first support member, a distal end, a length separating the proximal and distal ends, and a second fastening element coupled along the second support member length;
extending outwardly from the upper end of the first support member;
having a first position along a secondary support path defining a range of motion beginning with the distal end uncoupled from the first support member to a second position along the secondary support-path, the second position including the second support member configured to be wrapped from at least one of a dorsal side of user's wrist and a ventral side of a user's wrist to a plurality of locations on the outer surfaces of both the first support member and the second support member when the first support member is substantially encapsulating a portion of a user's wrist to provide a range of motion and pressure to a portion of a user's wrist, the range of motion and pressure corresponding to a select one of the plurality of locations on the outer surfaces of both the first support member and the second support member.

2. The hand and wrist brace according to claim 1, further comprising:
the substantially elastic material separating the inner and outer surfaces of the first support member.

3. The hand and wrist brace according to claim 1, wherein:
the body is substantially stretchable.

4. The hand and wrist brace according to claim 1, wherein the first support member further comprises:
a substantially planar orientation when in the first position along the wrist support path.

5. The hand and wrist brace according to claim 1, wherein:
the first and second fastening elements are removably-couplable, when in their respective second positions, with a hook-and-loop attachment.

6. The hand and wrist brace according to claim 1, wherein:

the second support member length is sufficiently-sized to substantially surround at least 50% of the circumferential outer surface of the first support member when in the second position.

7. The hand and wrist brace according to claim 1, wherein:
the second support member length is sufficiently-sized to substantially surround the circumferential outer surface of the first support member when in the second position at least once.

8. The hand and wrist brace according to claim 1, wherein the first support member further comprises:
a length separating the upper and lower ends, wherein the first support member length is less than the second support member length when the second support member is in the second position.

9. A hand and wrist, non-gloved, brace comprising:
a body free from any rigid splints coupled thereto, the body including:
a wrist support member having:
an inner surface and an outer surface;
a left end, a right end, a lower end, and an upper end;
a first fastening element coupled to at least one of the left end and right end;
a first position along a wrist support path with the left and right ends being uncoupled and a second position along the wrist support path with the first fastening element coupled to the outer surface of the wrist support member to substantially encapsulate a portion of a user's wrist; and
a second hand/wrist support member:
extending outwardly from the upper end of the wrist support member;
having an inner surface and an outer surface;
made of a substantially elastic material configured to provide pressure to an entire portion of a user's wrist;
having a proximal end directly coupled to the wrist support member, a distal end, and a length separating the proximal and distal ends;
having a second fastening element coupled to the distal end of the second hand/wrist support member;
having a first position along a secondary support path defining a range of motion beginning with the distal end uncoupled from the wrist support member to a second position along the secondary support path, the second position including the second support member configured to be wrapped from at least one of a dorsal side of user's wrist and a ventral side of a user's wrist to the outer surfaces of both the wrist support member and the second hand/wrist support member when the wrist support member is substantially encapsulating a portion of a user's wrist to provide a range of motion and pressure to a portion of a user's wrist, the range of motion and pressure corresponding to a select location on the outer surfaces of at least one of the wrist support member and the second hand/wrist support member.

10. The hand and wrist, non-gloved, brace according to claim 9, wherein:
the second hand/wrist support member length is sufficiently-sized to substantially surround at least 50% of the circumferential outer surface of the wrist support member when in the second position.

11. The hand and wrist, non-gloved, brace according to claim 9, wherein:
the second hand/wrist support member length is sufficiently-sized to substantially surround the circumferential outer surface of the wrist support member when in the second position.

12. The hand and wrist, non-gloved, brace according to claim 9, wherein:
the second fastening element is removably-couplable to a plurality of locations on the outer surfaces of the wrist support member and the second hand/wrist support member with a hook-and-loop attachment.

13. The hand and wrist, non-gloved, brace according to claim 9, wherein:
the inner and outer surfaces of the wrist support member are separated by the substantially elastic material.

14. The hand and wrist, non-gloved, brace according to claim 9, wherein:
the body is substantially stretchable.

15. The hand and wrist, non-gloved, brace according to claim 9, wherein the wrist support member further comprises:
a substantially planar orientation when in the first position along the wrist support path.

16. The hand and wrist, non-gloved, brace according to claim 9, wherein:
the second hand/wrist support member length is at least six inches when in the first position along the secondary support path.

17. A method of bracing and supporting a hand and wrist of a user, comprising the steps of:
providing:
a body free from any rigid splints coupled thereto, the body including:
a wrist support member having:
an inner surface, an outer surface, a left end, a right end, a lower end, and an upper end; and
a first position along a wrist support path with the left and right ends being uncoupled and a second position along the wrist support path with the left and right ends being coupled together; and
a second hand/wrist support member:
having an inner surface and an outer surface;
made of a substantially elastic material;
having a proximal end directly coupled to the wrist support member, a distal end, and a length separating the proximal and distal ends, the length being sufficiently-sized to substantially surround at least 50% of the circumferential outer surface of the wrist support member when in the second position;
extending outwardly from the upper end of the wrist support member; and
having a first position along a secondary support path defining a range of motion beginning with the distal end uncoupled from the wrist support member to a second position along the secondary support path with the second hand/wrist support being removably-couplable to the outer surfaces of both the wrist support member and the second hand/wrist support member when the first support member is substantially encapsulating a user's wrist;
placing the wrist support member and second hand/wrist support member in the first position;

positioning a portion the second hand/wrist support member between a web portion defined by an index finger and a thumb of a user's hand;

coupling the left and right ends of the wrist support member to substantially encapsulate a user's wrist; and coupling the second hand/wrist support member to a select location on the outer surface of the second hand/wrist support member to provide a range of motion and pressure to a user's wrist, the range of motion and pressure corresponding to the select location on the outer surface of the second hand/wrist support member.

18. The method according to claim 17, wherein:

the second hand/wrist support member length is sufficiently-sized to substantially surround at least 50% of the outer surface of the wrist support member when in the second position.

* * * * *